United States Patent [19]

Stella et al.

[11] Patent Number: 4,960,790

[45] Date of Patent: Oct. 2, 1990

[54] DERIVATIVES OF TAXOL, PHARMACEUTICAL COMPOSITIONS THEREOF AND METHODS FOR THE PREPARATION THEREOF

[75] Inventors: Valentino J. Stella, Lawrence; Abraham E. Mathew, Lenexa, both of Kans.

[73] Assignee: University of Kansas, Lawrence, Kans.

[21] Appl. No.: 321,152

[22] Filed: Mar. 9, 1989

[51] Int. Cl.$^5$ .................. A61K 31/335; C07D 305/14
[52] U.S. Cl. .................... 514/449; 546/196; 548/525; 549/510; 514/320; 514/422; 514/908
[58] Field of Search ............... 549/510, 511; 514/449, 514/908, 320, 422; 548/525; 546/196

[56] References Cited

U.S. PATENT DOCUMENTS 4,163,058 7/1979 Stella et al. .................... 548/312
4,650,803 3/1987 Stella et al. .................... 514/291

OTHER PUBLICATIONS

A. L. Lehninger, "Biochemistry," 2nd ed., pp. 72-76, Worth Publishers, Inc. (1975).
Wiernik et al., Cancer Research 47, 2486-2493, May 1, 1987.
Schiff et al., Proc. Natl. Acad. Sci. U.S.A., vol. 77, No. 3, pp. 1561-1565 (3/80).
Mellado et al., Biochemical and Biophysical Research Communications, vol. 124, No. 2, pp. 329-336, 1984.
Magri et al., J. Org. Chem., 51, 797-802, 1986.
Manfredi et al., Pharmac. Ther., vol. 25, pp. 83-125 (1984).
Magri et al., Journal of Natural Products, vol. 51, No. 2, pp. 298-306, Mar.-Apr. 1988.
"In Vivo Cancer Models", NIH Publication No. 84-2635, Feb. 1984.

Primary Examiner—Richard L. Raymond
Assistant Examiner—Mark W. Russell
Attorney, Agent, or Firm—Birch, Stewart, Kolasch & Birch

[57] ABSTRACT

Derivatives of taxol represented by the formula

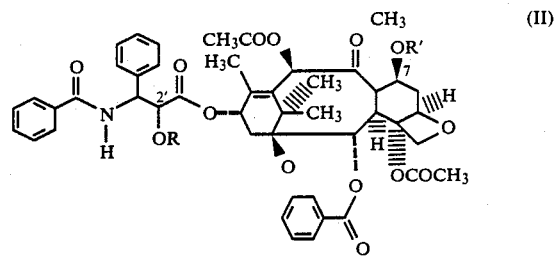

(II)

wherein R and R' are each H or the residue of an amino acid selected from the group consisting of alanine, leucine, isoleucine, saline, phenylalanine, proline, lysine and arginine or a group of the formula

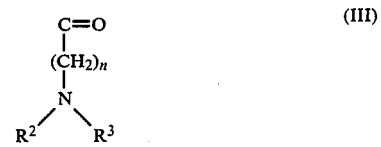

(III)

wherein n is an integer of 1 to 3 and $R^2$ and $R^3$ are each hydrogen on an alkyl radical having from one to three carbon atoms or wherein $R^2$ and $R^3$ together with the nitrogen atom to which they are attached form a saturated heterocyclic ring having four to five carbon atoms, with the proviso that at least one of R and $R^1$ is not hydrogen, are provided together with pharmaceutical compositions of such derivatives. The taxol derivatives have increased water solubility as compared to taxol, and have excellent antitumor activity.

34 Claims, No Drawings

DERIVATIVES OF TAXOL, PHARMACEUTICAL COMPOSITIONS THEREOF AND METHODS FOR THE PREPARATION THEREOF

BACKGROUND AND FIELD OF THE INVENTION

The present invention is directed to derivatives of taxol which have improved water solubility as compared to taxol, and exhibit excellent antitumor activity. The compounds are particularly useful for the treatment of the same cancers for which taxol has been shown active, including human lung tumors, melanoma, leukemia, mammary tumors, and colon cancer.

Taxol is a known diterpenoid, sesquiterpene which was originally isolated from the stem bark of the western yew, *Taxus brevifolia*, and has the following structure:

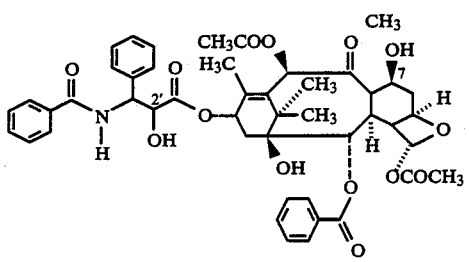

Taxol has been shown to possess potent antitumor activity against a wide variety of tumors. This compound, however, is only very slightly soluble in water and this has created significant problems in developing suitable pharmaceutical formulations useful for human therapy. Some formulations of taxol for injection or I.V. infusion have been developed primarily utilizing cremophore EL ® as the drug carrier to overcome the low water solubility problems of taxol. Cremophore, however, is itself somewhat toxic causing idiosyncratic histamine release and anaphylactoid like response, so the use of this carrier is not a desirable solution to the problem of developing good formulations of taxol.

The present inventors, therefore, have investigated the development of derivatives of taxol which would be more water soluble than taxol, but would also exhibit the same or similar excellent antitumor and cytotoxic activity of taxol.

SUMMARY AND OBJECTS OF THE INVENTION

It is, therefore, one object of the present invention to develop derivatives of taxol which exhibit good antitumor activity and are water soluble.

It is another object of the invention to develop formulations of taxol derivatives which utilize non-toxic carriers, thereby avoiding the use of toxic carriers, such as cremophore.

It is a further object of the invention to develop taxol derivatives which exhibit good stability at pH levels suitable for making pharmaceutical formulations (pH 3 to 4), but quickly break down in vivo at physiological pH (pH 7.4) to potentially act as a taxol pro-drug.

These and other objects of the invention are realized by the development of derivatives of taxol which have good antitumor activity and good water solubility.

DETAILED DESCRIPTION OF THE INVENTION

The novel derivatives of taxol of the present invention can, in general, be described as 2' and/or 7-position esters of taxol, represented by the following formula:

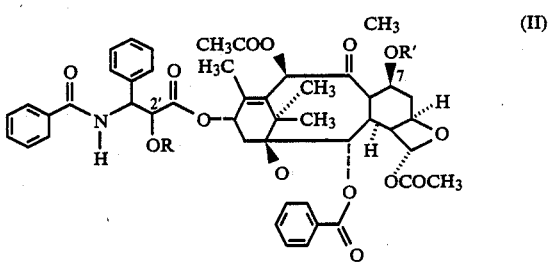

wherein R and R' are each H or the residue of an amino acid selected from the group consisting of alanine, leucine, isoleucine, valine, phenylalanine, proline, lysine and arginine or a group of the formula

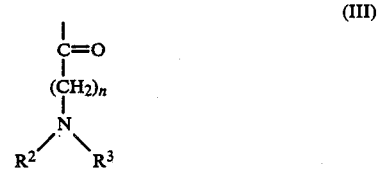

wherein n is an integer of 1 to 3 and $R^2$ and $R^3$ are each hydrogen or an alkyl radical having from one to three carbon atoms or wherein $R^2$ and $R^3$ together with the nitrogen atom to which they are attached form a saturated heterocyclic ring having four to five carbon atoms, with the proviso that at least one of R and $R^1$ is not hydrogen.

In the above formula (III), when $R^2$ and/or $R^3$ are other than hydrogen, these compounds can be considered, and are sometimes hereinafter referred to as "alkylated amino acids". Thus, the compounds of the formula (I) can broadly be considered as 2' and/or 7-position esters of taxol with amino acids or alkylated amino acids.

The invention thus includes (a) derivatives esterified at the 2'-hydroxyl group of taxol, (b) derivatives esterified at the 7-hydroxyl group of taxol, and (c) derivatives esterified at both the 2'- and 7-position hydroxyl groups.

Among the compounds encompassed by the above general formula (I), the following specific compounds can be considered preferred compounds of the invention.

1. 2'(N,N-diethylaminopropionyl)taxol
2. 2'(N,N-dimethylglycyl)taxol
3. 7(N,N-dimethylglycyl)taxol
4. 2',7-di-(N,N-dimethylglycyl)taxol
5. 7(N,N-diethylaminopropionyl)taxol
6. 2',7-di(N,N-diethylaminopropionyl)taxol
7. 2'-(L-glycyl)taxol 8. 7-(L-glycyl)taxol
9. 2',7-di(L-glycyl)taxol
10. 2'-(L-alanyl)taxol
11. 7-(L-alanyl)taxol
12. 2',7-di(L-alanyl)taxol
13. 2'-(L-leucyl)taxol
14. 7-(L-leucyl)taxol
15. 2,7-di(L-leucyl)taxol
16. 2'-(L-isoleucyl)taxol
17. 7-(L-isoleucyl)taxol
18. 2',7-di(L-isoleucyl)taxol
19. 2'-(L-valyl)taxol
20. 7-(L-valyl)taxol
21. 2',7-di(L-valyl)taxol
22. 2'-(L-phenylalanyl)taxol
23. 7-(L-phenylalanyl)taxol
24. 2',7-di(L-phenylalanyl)taxol
25. 2'-(L-prolyl)taxol
26. 7-(L-prolyl)taxol
27. 2',7-di(L-prolyl)taxol
28. 2'-(L-lysyl)taxol
29. 7-(L-lysyl)taxol
30. 2',7-di(L-lysyl)taxol
31. 2'-(L-glutamyl)taxol
32. 7-(L-glutamyl)taxol
33. 2',7-di(L-glutamyl)taxol
34. 2'-(L-arginyl)taxol
35. 7-(L-arginyl)taxol
36. 2',7-di(L-arginyl)taxol

PREPARATION PROCEDURES

The present inventors have found that the chemical reactivity characteristics of the 2'- and 7-position hydroxyl groups of taxol, specifically the 2'-hydroxyl is more chemically reactive than the 7-hydroxyl group. This observation has then been utilized to direct the position of derivatives in the preparation procedures.

A. Preparation of 2'-ester derivatives

The 2'-ester derivatives can be prepared by one of two methods, depending upon whether the derivative is to be with an amino acid or with an alkylated amino acid.

For preparing esters of alkylated amino acids, the following reaction scheme is followed:

Scheme I alkylated amino acid + taxol ——→ 2'-ester taxol derivative

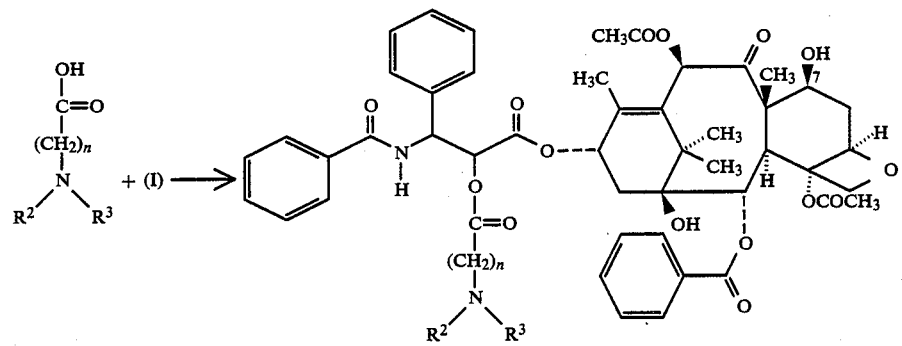

wherein n, $R^2$ and $R^3$ are as defined above.

For preparing esters of amino acids, the following reaction scheme is followed:

Scheme II

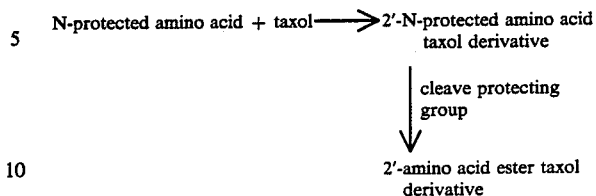

In both of the above reaction schemes (Schemes I and II), the reaction of the alkylated or protected amino acid is conducted in the presence of a condensing reagent, and with or without the additional presence of a catalyst, preferably at room temperature.

Suitable condensing reagents include carbodiimides, such as dicyclohexyl carbodiimide (DCC).

Suitable catalysts include 4-dimethylamino-pyridine (DMAP) and pyridine.

In reaction Scheme (II), various known amino protecting groups can be utilized and commercially available protected amino acids can be utilized as the starting materials. Amino acids protected with t-BOC, FMOC or carbobenzyloxy (CBZ) can be utilized. Amino acids protected with t-BOC or FMOC groups are preferred. Although the deprotection of t-BOC group on the 2'-esters using aqueous formic acid and other organic acid resulted in the degradation of the product and also stereochemical modification, the use of 99% formic acid gave better results. In the case of FMOC protected amino acid esters the product recovery depends on the work up conditions. Thus, in the final deprotection step, the conditions utilized to remove the t-BOC protecting group can cause undesirable modifications at the 7-position free hydroxyl group of the taxol molecules. These undesirable modifications appear to consist of stereochemical modifications of the molecule.

As examples, N-protected alanine compounds can be represented as below:

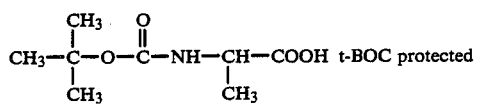

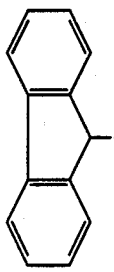 —CH₂—O—C(=O)—NH—CH(CH₃)—COOH  FMOC protected

As noted above, the inventors have found that the 2'-hydroxyl of taxol is more chemically reactive than the 7-hydroxyl group. Thus, in both Schemes I and II above, substitution or esterification is directed to the 2'-position by reacting the alkylated or N-protected amino acid with taxol in a 1:1 or slightly greater than 1:1 molar ratio. Such a reaction of equal molar amounts results in the production of a large excess of the 2'-ester taxol derivative, although some small amount of a 7-ester taxol derivative may be produced as a side product.

B. Preparation of 7-position esters

Scheme III

Since the 2'-hydroxyl of taxol is more reactive than the 7-position hydroxyl, this esterification requires the use of a procedure different from that used to prepare the 2'-derivatives. Thus, to prepare the 7-position esters, a procedure is utilized whereby the 2'-hydroxyl is first protected or blocked, then the 7-position hydroxyl is esterified and then the 2'-protecting or blocking group is removed.

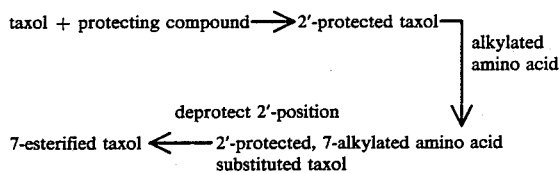

A variety of blocking groups can be utilized to block the 2-position of taxol, such as those known in the art. Using one example of a blocking group and using an alkylated amino acid as an example, the reaction Scheme (III) can also be summarized as follows:

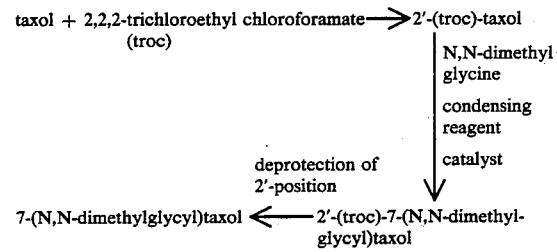

In the above reaction scheme, the reaction of the 2'-troc-taxol and the alkylated amino acid is conducted in the presence of a condensing reagent and a catalyst. Suitable condensing reagents and catalysts are the same as discussed above for Schemes I and II.

Deprotection of the 2'-(troc.) taxol can be conducted, for example, by utilizing a mixture of zinc and acetic acid.

Scheme IV

As an alternative procedure, 7-substituted taxol derivatives can also be prepared by a procedure which first reacts taxol with 2-3 equivalents of an N-blocked amino acid to produce at 2', 7-disubstituted taxol, both the 2'- and 7-position amino acids are deprotected, and the 2'-position amino acid is then cleaved. This procedure can be represented as follows, using t-BOC protected alanyl as an exemplary blocked amino acid.

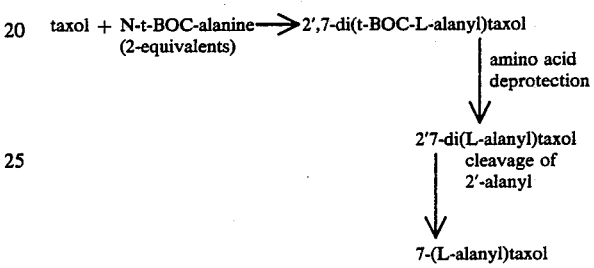

In this procedure, similar to Scheme III, the reaction of taxol and the protected amino acid is conducted in the presence of a condensing reagent and a catalyst. Deprotection of the amino acids is conducted under a known amino acid deprotection method, such as mild acid treatment with, for example, formic acid.

Cleavage of the 2'-amino acid is conducted by adjusting the pH of the 2',7-(amino acid)taxol solution to pH 7-7.4, for example by mixture of the 2',7-di(amino acid) taxol in a phosphate buffer at pH 7-7.4. Adjustment of the pH in this manner cleaves the 2'-amino acid to produce the desired 7-(amino acid)taxol.

Thus, for example, taxol is allowed to react with 2-3 mol. equivalent of N-protected amino acid (t-boc, CBZ or FMOC protected) in methylene chloride in the presence of DCC and a catalytic amount of 4-dimethylaminopyridine. In this manner, the protected amino acid is introduced at 2' and 7-position. The protecting groups are removed by appropriate deprotecting agent (e.g., acid, mild base or hydrogenolysis). The 2',7-bis amino acid derivative of taxol is allowed to stand in phosphate buffer at neutral pH for 24-48 hours, whereby selective deprotection at the 2'-position occurs to yield the 7-substituted derivative of taxol.

A similar reaction scheme could also be utilized to produce 7-substituted taxol derivatives with alkylated amino acids. Such a reaction would be similar as above, except substituting the N-protected amino acid with the desired alkylated amino acid and eliminating the deprotection step. This scheme can be represented as follows:

Scheme V taxol + alkylated amino acid ⟶ 2',7-(disubstituted)taxol
(2-equivalents)

↓ cleavage of 2'-alkylated amino acid 7-(substituted)taxol

C. Preparation of 2',7-disubstituted Taxol Derivatives

The disubstituted derivatives can be prepared by utilizing the above procedures, or parts of the above procedures. These procedures can be outlined as follows:

Scheme VI: substitution with alkylated amino acids taxol + alkylated amino acid ⟶ 2'7-(disubstituted alkylated
(2–3 equivalents)      amino acid)taxol Scheme VII: substitution with amino acids taxol + alkylated amino acid ⟶ 2',7-(disubstituted alkylated
(2–3 equivalents)      amino acid)taxol ↓ amino acid deprotection 2',7-(disubstituted amino acid)taxol Scheme VI basically is the same as Scheme I above, except that the reaction takes place with 2 equivalents of the alkylated amino acid. In addition, although Scheme I can be conducted in the presence or absence of a catalyst, the process of Scheme VI requires the presence of a catalyst due to the reduced chemical reactivity of the taxol 7-position hydroxyl group.

Scheme VII is basically the same as above Scheme II. However, it was noted above that in Scheme II, FMOC is the preferred protecting group in order to avoid stearic modifications at the 7-position during the deprotection step. This problem, however, does not occur in the reaction Scheme VII since the 7-position hydroxyl group is not free. Thus, various known protecting groups can be used, including both t-BOC and FMOC.

It is believed that one of ordinary skill in the art can, using the above description prepare the full scope of the compounds of the present invention. The following, however, are presented as preferred specific embodiments as illustrative of the preparation procedures.

EXAMPLE I

2'-(N,N-Dimethylglycyl)taxol or a salt thereof

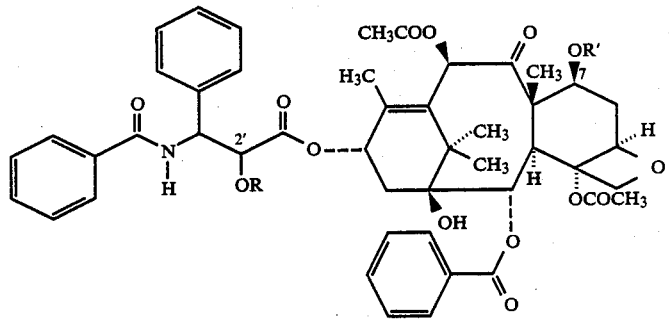

1. $R = O=\overset{|}{C}-CH_2-N(CH_3)_2$,  $R' = H$

2. $R = O=\overset{|}{C}-CH_2-N(CH_3)_2$,  $R' = H$
   $\cdot CH_3SO_3H$ (a) Compound 1—2'-(N,N-dimethylglycyl)taxol To a solution of taxol (0.21 g, 0.246 mmol) and N,N-dimethylglycine (0.0254 g, 0.246 mmol) in anhydrous methylene chloride (12 ml), 1,3-dicyclohexylcarbodiimide (0.15 g, 0.72 mmol) and 4-dimethylaminopyridine (0.025 g, 0.2 mmol) are added. The reaction mixture is stirred at anhydrous conditions for one day. Another 50 mg of DCC is added and the stirring is continued another six hours. The reaction mixture is filtered and the filtrate is evaporated under nitrogen. The residue is chromatographed over silanized silica gel (35 g, 26 cm) and eluted successively with ethyl acetate:petroleum ether 1:1 and ethyl acetate. The ethyl acetate:petroleum ether fractions upon slow evaporation, a solid appears which is filtered. The mother liquor is concentrated and petroleum ether is added till turbidity appeared and set aside to obtain more compound. The total recovery is 0.14 g (61%). M.p. 168°–71° (dec). In the NMR spectrum of compound 2 (300 MH, CDCl$_3$) the resonances of the 2' proton is shifted from 4.71 ppm in taxol to 5.59 ppm. This is consistent with esterification at 2'-position. All other resonances of the spectrum are in agreement with the assigned structure. HPLC purity 98–99.5%. Mass spectrum: (FAB) m/e 939. (M+H)+ Elemental analysis: calculated for $C_{51}H_{58}N_2O_{15}$; C, 65.26, H, 6.22, N, 2.98; Found C, 65.16, H 6.28, N, 3.13%.

(b) Compound 2—Methanesulphonic acid salt of 2'-(N,N-dimethylglycyl)taxol

2'-(N,N-Dimethylglycyl)taxol (0.06 g, 0.064 mmol) is dissolved in t-butanol (2 ml) and water (1.5 ml). The mixture is cooled to ~5° and methanesulphonic acid (3.1 ml, 2 mg/ml, 0.0645 mmol) is added dropwise and the mixture is stirred at 0°-5° for one minute and filtered through 20 um filter (millipore) to a flask cooled in a dry ice-isopropanol mixture. The solution is freeze dried to get 0.058 g product, (88%), M.p. 170°-173°. Elemental analysis: Calculated for $C_{52}H_{62}N_2SO_{18}.2H_2O$; C, 57,83, H, 6.27, N, 2.6; Found, C. 57.49, H, 6.06, N, 2.73%.

| Physical properties | |
|---|---|
| Mol. wt.: | 1035 |
| M.P.: | 170-173 (Dec.) |
| Solubility: | 15 mg/mL (Slightly Hazy) |
| | 2 mg/mL (Clear) |

Chemical Stability Studies

The compound was subjected to stability studies according to the following procedures.

Stabilities of derivatives at various pHs were studied at 25° and 37°. The plasma studies were conducted at 37° in rat and human plasma. Human plasma was obtained from Watkins Hospital and rat plasma was obtained from the Animal Care Unit of the University of Kansas. The derivative concentration used was around 20-25 μg/ml. A stock solution of the compound was prepared at 0.8-1.0 mg/mL and was added to plasma to give the desired concentration (20-25 μg/mL). One hundred microliter samples were removed and was quenched with 250 uL. acetonitrile and centrifuged to precipitate the plasma proteins. The degradation kinetics were studied by HPLC plotting peak area vs. time. The $t_{90}$ and $t_{50}$ were calculated. Both chemical and plasma studies were followed by high performance liquid chromatography using a RP-8 column (15 cm) and a precolumn (5 cm). The detector was set at 227 nm. The mobile phase consisted of 0.02M acetate (pH 5): acetonitrile 50:50 or 35:65 and the flow rate ranged from 1-1.5 mL/min or the same solvents containing 0.001M tetrabutylammoniumydrogensulphate and a flow rate of 1 mL/min.

In the stability studies, the disappearance of the compound peak resulted in the formation of a peak having a retention time equal to that of taxol. The identity of this peak was further confirmed by the degradation studies of the new derivatives. Thus, 2'(DMG) taxol was incubated with water at 37° and the product was concentrated and purified by preparative TLC. The product after purification was analyzed by HPLC and spectroscopic methods. The product showed a molecular ion peak at m/e 860 (M+Li)+, indicating that the product is taxol.

| HPLC Operating Conditions: | |
|---|---|
| Column: | RP-8, 150 mm length, 4.6 mm id |
| mobile phase: | 0.02 M Acetate (pH5): Acetonitrile 50:50: |
| Detector: | Kratos Spectroflow 757 |
| Flow rate: | 1 mL/min |
| Ret. Time: | 11.2 mL compound 2 |
| | 5.5 mL taxol |
| Chemical Stability Results: | |
| conditions | $t_½$ (hrs) |
| 0.02 M Acetate (0.1 mg/mL) | |
| (pH 3.5, 25° C.) | 96.2 |
| (pH 4.5, 25° C.) | 55.4 |
| water (2 mg/mL) | |
| (pH 3.8, 37° C.) | 89.8 |
| Plasma Stability, 37° C.: | |
| conditions | $t_½$ (min) |
| rat plasma (20 μg/mL) | 3.05 |
| dog plasma (20 μg/mL) | 121.6 |
| human plasma (20 μg/mL) | 198.6 |

EXAMPLE II

Salts of 2'(N,N-diethylaminopropionyl)taxol

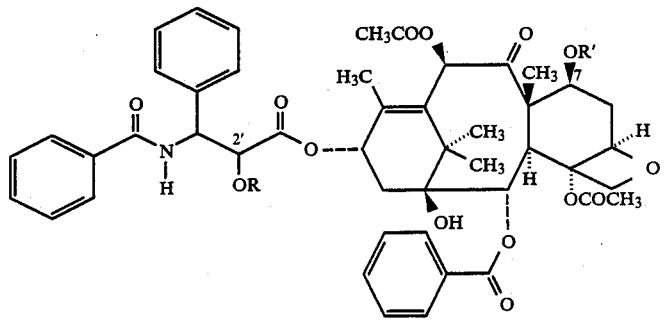

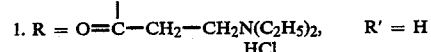

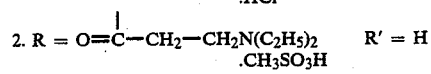

(a) Compound 3—HCl salt of 2'-(3-(N,N-diethylamino)propionyl)taxol

To a solution of taxol (0.12 g, 0.14 mmol) in $CH_2Cl_2$ (12 ml) containing N,N-diethylaminopropionic acid hydrochloride (0.025 g, 0.145 mmol) is added 1,3-dicyclohexylcarbodiimide (0.08 g, 0.38 mmol) and 4-dimethylaminopyridine (0.01 g, 0.081 mmol). The resulting mixture is stirred at room temperature for 24 hours. The reaction mixture is filtered and the filtrate is evaporated under nitrogen. The crude material is chromatographed over a silanized silica gel column (18 g, 22 cm) and eluted successively with ethyl acetate:petroleum ether 1:2, ethyl acetate:petroleum ether 1:1 and ethyl acetate. The ethyl acetate:petroleum ether fractions on slow evaporation formed a solid precipitate which is filtered.

The mother liquors containing product are combined, concentrated and petroleum ether is added to turbidity and set aside. The product is filtered to obtain 0.068 g product (48%). M.P. 188°-191° C. mass spectrum (FAB) m/e 981 [M+H]+. NMR (300 Hz, CDCl₃) indicated that the resonances of the 2, proton shifted from 4.71 ppm in taxol to 5.53 ppm. The N-ethyl groups showed methyl resonance at 1.0 ppm and the $CH_2$ resonance at 2.52 ppm. All other resonances characteristic of the expected compound were observed. Elemental analysis calculated for $C_{54}H_{65}ClN_2O_{15}$, C, 63.73, H, 6.43, N, 2.75; Found C, 64.84, H, 6.84, N, 2.89%.

| Physical Properties (For compound 3) | |
|---|---|
| Mol. Wt: | 1017.56 |
| M.P.: | 186-189° C. (dec.) |
| Solubility | ~0.8 mg/mL |
| HPLC Conditions | |
| Column: | RP-8, 150 mm length, 4.6 mm i.d. |
| mobile phase: | 0.02 M Acetate (pH 5): Acetonitrile 35:65 |
| Detector: | Kratos Spectroflow 757 |
| Flow rate | 1.5 mL/min |
| Ret. Volume | 16.71 mL (compound 3) |
| Chemical Stability: | |
| Conditions | $t_{\frac{1}{2}}$ (hrs.) |
| 0.02 M Acetate (0.01 mg/mL, pH 3.5, 25° C.) | 438.6 |
| 0.02 M Phosphate (0.02 mg/mL, pH 7.4, 25° C.) | 0.25 |
| Plasma Stability, 37° C. | |
| Conditions | $t_{\frac{1}{2}}$ (min.) |
| Human plasma | 4.2 |

(b) Compound 4—Methanesulphonic acid salt of 2'(N,N-diethylaminopropionyl)taxol

In order to prepare the methanesulphonic acid salt of N,N-diethylaminopropionic acid, 10 g of QAE-sephadex (Pharmacia) was wet with 0.1M NaCl for 75 Hrs. and 75% of that material was poured to a column. The column was washed with distilled water (700 mL). The column was equilibrated with 500 mL CH₃SO₃Na (prepared from 0.5M methanesulphonic acid and 0.5M sodium hydroxide and titrated to pH 6). The complete disappearance of Cl— was assessed by collecting the eluate and testing for Cl— by the addition of a few drops of 1% silver nitrate in a few drops of nitric acid. The column was further washed with distilled water till neutral.

2.5 g of N,N-diethylaminopropionic acid HCl salt in 15 mL water was poured over the column and eluted with water. Four 50 mL fractions were collected. The first few fractions contained the product. These fractions were combined and solvent was removed. The residue was dissolved in methylene chloride-ethanol mixture and dried over magnesium sulphate and solvent was removed to get 3.1 g product. It was precipitated from ethanol and ether to yield 2.6 g methanesulphonic acid salt of N,N-diethylaminopropionic acid.

To a solution of taxol (0.05 g, 0.058 mmol) and N,N-diethylaminopropionic acid methanesulphonic acid salt (0.014 g, 0.058 mmol) in methylenechloride (10 mL) is added 1,3-dicyclohexylcarbodiimide (0.061 g, 0.3 mmol). The mixture is stirred at room temperature for 24 hours. The reaction mixture is filtered and the filtrate is evaporated under nitrogen. The residue is chromatographed over a silanized silica gel column and eluted with ethyl acetate:petroleum ether 1:1 and ethyl acetate. The ethyl acetate:petroleum ether fractions on slow evaporations yielded 0.048 g of product (74%). M.p. 170°-74° C.

| Physical properties: | |
|---|---|
| Mol. wt. | 1077.12 |
| M.p. | 170-74 |
| Solubility | >10 mg/mL |
| HPLC purity | >99% |
| Chemical stability: | |
| Conditions | $t_{\frac{1}{2}}$ (hours) |
| 0.02 M acetate (pH 4.5, 25° C.) | 305 |
| 0.02 M acetate (pH 5.5, 25° C.) | 20.7 |

EXAMPLE III

Preparation of 7-(N,N-dimethylglycyl)taxol or a salt thereof

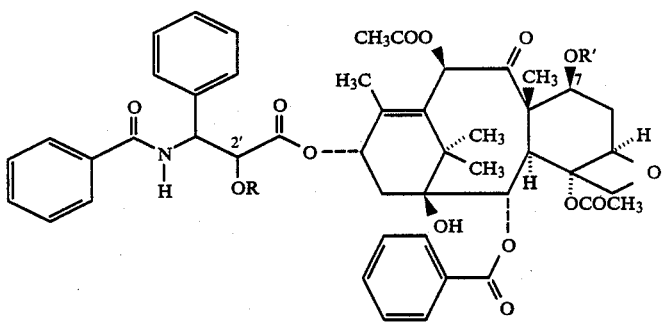

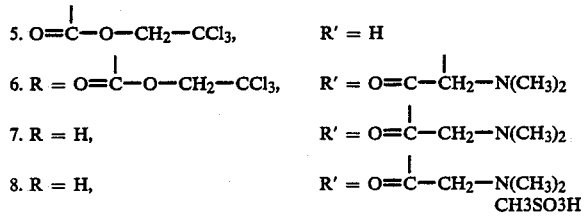

(a) 2'-(troc)taxol (Compound 5)

Taxol (0.27 g, 0.316 mmol) is dissolved in CH$_2$Cl$_2$ (10 ml) and pyridine (1.5 mL). The reaction mixture is cooled to −20- (−25°) and 2,2,2,-trichloroethyl chloroformate (80 ul) is added. The reaction mixture is stirred at this temperature for three hours. Another 25 μl of chloroformate is added and the reaction mixture is stirred overnight. The reaction mixture is diluted with CH$_2$Cl$_2$ (50 ml) and washed successively with 0.1N HCl (25 ml×2) and 0.05M cold NaHCO$_3$ (25 mL×1) and water. The organic extract is dried over anhydrous MgSO$_4$, and the solvent is removed. The crude material is purified by preparative TLC over silanized silica gel plates and developed in ethyl acetate-petroleum ether 1:3 and a band above taxol is cut and eluted with ethyl acetate and solvent is removed to get 0.32 g (97%), m.p. 221°–226° (dec., soft 160°).

(b) 2'-(Troc)-7-(N,N-dimethylglycyl)taxol (Compound 6)

A mixture of 2'-(troc)taxol (0.27 g, 0.262 mmol) and N,N-dimethylglycine (0.054 g, 0.524 mmol) is dissolved in CH$_2$Cl$_2$ (15 mL). To this solution 1,3-dicyclohexylcarbodiimide (0.215 g, 1.04 mmol) and 4-dimethylaminopyridine (0.025 g, 0.2 mmol) are added and the mixture is stirred at room temperature for two days. The reaction mixture is filtered and the solvent is removed. The crude material is purified by preparative TLC over silanized silica gel plates and developed in ethyl acetate:petroleum ether 1:1. A band below taxol (Rf 0.47, ethyl acetate-petroleum ether 1:1) is cut and eluted with ethyl acetate, and solvent is removed to get 0.26 g of product (89%). M.p. 176°–180° C. (dec.). Elemental analysis, Calculated for C$_{54}$H$_{60}$Cl$_3$N$_2$O$_{17}$, C, 58.16, H, 5.42, N, 2.51; Found, C 58.68, H, 6.00, N, 3.18%.

(c) 7-(N,N-Dimethylglycyl)Taxol (Compound 7)

To a solution of 2'-(troc)-7-(N,N-dimethylglycyl)taxol (0.335 g, 0.3 mmol) in methanol-acetic acid 9:1 (12 mL) zinc dust (0.275 g) is added and the mixture is stirred at room temperature for 25 minutes and filtered. The filtrate is concentrated to ~1 mL and diluted with CH$_2$Cl$_2$ (35 mL) and washed successively with 0.01M HCl (20 mL×2), 0.01M cold NaHCO$_3$ and water. The organic extract is dried over anhydrous Na$_2$SO$_4$ and solvent is removed to get 0.24 g product. This compound is purified by preparative TLC over silanized silica gel plates (20×20, 3 Nos) and developed in CH$_2$Cl$_2$:ethyl acetate 7:1. The band corresponding to 7-(DMG)taxol (Rf 0.35) is cut and eluted with ethyl acetate and ethanol and solvent is removed to get 0.19 g of product (68%). M.P. 180–185 (dec. softens ~140° C.). Mass spectrum (FAB) m/e 939 [M+H]$^+$. In the NMR spectrum (300 MHz, CDCl$_3$) the resonances of the 7-H at 4.33 ppm in taxol appeared as a doublet of doublet at 5.65 ppm. The N-(CH$_3$)$_2$ resonance appeared as a singlet at 2.35 ppm. The methylene group of the glycinate was found at 3.16 ppm.

(d) Methanesulphonic acid salt of 7-(dimethylglycyl)taxol (Compound 8)

7-(Dimethylglycyl)taxol (0.65 g, 0.069 mmol) is dissolved in t. butanol (2.5 mL) and water 1 mL). The solution is cooled to 5°–10° and methanesulphonic acid (3.36 mL, 2 mg/ML, 0.0697 mmol) is added. The mixture is stirred for two minutes and filtered through a millipore filter to a flask cooled in ice. The filtrate is freeze dried to give 0.066 g of product (94%). Mp. 164–168 (dec). Elemental analysis: Calculated for C$_{52}$H$_{62}$N$_2$O$_{18}$S.2H$_2$O; C, 58.29, H, 6.19, N, 2.6; Found, C, 58.05, H, 6.00, N, 1.72.

| Physical Properties: | |
|---|---|
| Mol. Wt.: | 1035 |
| M.P.: | 164–168° C. |
| Solubility: | >2 mg/mL |
| HPLC Conditions: | |
| Column: | RP-8, 150 mm length, 4.6 mm i.d. |
| Mobile phase: | 0.02 M Acetate (pH 5): Acetonitrile 35:65 |
| Detector: | Kratos Spectroflow 757 |
| Flow rate: | 1.5 mL/min |
| Ret. Volume: | 15.07 mL (Compound 8) |
| Chemical Stability: | |
| conditions | t$_{\frac{1}{2}}$ (hrs.) |
| 0.02 M Acetate (pH 3.5, 25° C.) | 3397 |
| 0.02 M Acetate (pH 4.5, 25° C.) | 1719 |
| 0.02 M Phosphate pH 7.4 (25° C.) | 33.8 hours |
| Plasma Stability, 37° C.: | |
| conditions | t$_{\frac{1}{2}}$ (hrs.) |
| rat plasma (20 μg/mL) | 17.3 |
| human plasma (20 μg/mL) | 27.7 |
| human plasma (10 μg/mL) | 24.4 |

EXAMPLE IV

Preparation of 2′,7-(Dimethylglycyl)taxol

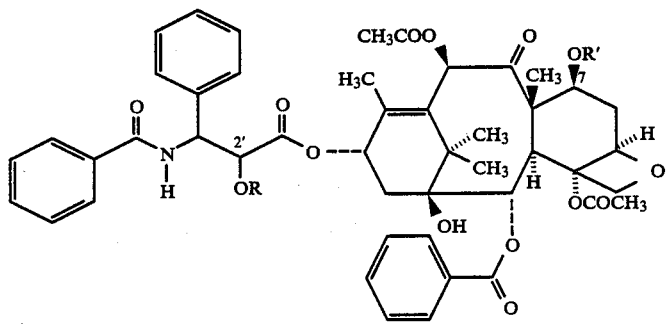

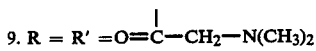

9. $R = R' = O=\overset{|}{C}-CH_2-N(CH_3)_2$

Taxol (0.06 g, 0.0702 mmol) is dissolved in anhydrous methylene chloride (5 mL) and N,N-dimethylglycine (0.015 g, 0.145 mmol) is added to it. To this mixture 1,3-dicylcohexylcarbodiimide (0.08 g, 0.388 mmol) and 4-dimethylaminopyridine (0.008 g, 0.065 mmol) are added. The reaction mixture is stirred at room temperature for 24 hours and filtered. Solvent is removed from the filtrate The residue is purified by preparative TLC on silanized silica gel plates and developed in ethyl acetate-petroleum ether 1:1. A band (Rf 0.17) above dimethylaminopyridine is scraped out and eluted with an ethylacetate and ethanol mixture and the solvent is removed. The residue is recrystallized from ethylacetate-petroleum ether to get 0.046 g of product (64%). M.p. 194°–198° C. Mass spectrum: m/e 1024. (M+). In the NMR spectrum (300 MHz, CDCl$_3$) the C$_2$-proton (4.71 ppm) and C7-proton (4.33 ppm) shifted to 5.5 ppm and 5.6 ppm respectively showing esterification at 2′ and 7-position. Also the N-CH$_3$ proton appeared as a singlet at 2.3 ppm.

| Elemental analysis calculated for $C_{55}H_{66}N_3O_{16}$ | |
|---|---|
| C 63.39 | Found C 63.00 |
| H 6.48 | H 6.98 |
| N 4.03 | N 3.98 |

Synthesis of dimethanesulphonic acid salt of 2′7-(N,N-dimethylglycyl)taxol

To a solution of 2,7-(dimethylglycyl)taxol (60 mg, 0.0585 mmol) in t-butanol (2 mL) and water (1 mL) cooled to 0°–5° C. is added methanesulphonic acid (11.37 mg, 3.79 mL, 0.117 mmol). The mixture is stirred at 0°–5° C. for 2 minutes and filtered through a millipore filter (0.2 μM) and the filtrate is freeze dried to get 62 mg product. M.P. 160°–63° C.

| Physical Properties | |
|---|---|
| Mol. Wt. | 1217 |
| M.P. | 160–163° C. (dec.) |
| Solubility | >10 mg/ml |
| HPLC purity | ~96% |
| HPLC Operating Conditions. | |
| Column: | RP-8, 150 mm, 4.6 mm ID |
| Mobile phase: | 0.02 M acetate (pH5): Acetonitrile 50:50 containing 0.005 M TBA |
| Detector: | Kratos spectroflow 757 |
| Flow rate: | 1 mL/Min. |
| Ret. Volume: | 6.64 mL |
| | 5.8 mL (taxol) |

EXAMPLE V

Preparation of 7-(-L-alanyl)taxol or salt thereof (a) 2′,7-Di(t.Boc.-L-alanyl)taxol To a solution of taxol (0.21 g, 0.246 mmol) and N-t.Boc-L-alanine (0.14 g, 0.739 mmol) in methylene chloride (15 mL) is added, 1,3-dicyclohexylcarbodiimide (0.25 g, 1.21 mmol) and dimethylaminopyridine (0.025 g, 0.20 mmol). The mixture is stirred at room temperature for 24 hours and filtered. The residue is chromatographed over silanized silica gel column (20 g, 14 cm) and eluted with ethylacetate: petroleum ether 1:1 and ethyl acetate. The ethyl acetate-petroleum ether fractions containing the disubstituted derivative are pooled, and the solvent is removed to give 0.27 g compound (92%). M.P. 158°–161° C. (dec.)

(b) 7-(L-Alanyl)taxol 2,7-di-(t.Boc.-L-alanyl)taxol (0.29 g, 0.242 mmol) and formic acid (2 mL) are mixed and stirred at room temperature for 40 minutes and excess formic acid is removed under nitrogen. The residue was dissolved in ethanol and petroleum ether was added. The solid was filtered to yield 0.27 g 2′,7-di(alanyl)taxol.

The crude dialanyl derivative thus obtained is taken in acetonitrile (4 mL) and phosphate buffer (0.02M, pH 7.4, 50 mL) and the mixture is stirred at room temperature for 12 hours. The pH of the solution is raised to 6.8 using a few mL of 5% Na$_2$HPO$_4$. The cloudy solution is stirred at room temperature for another 8 hours. The reaction mixture is diluted with methylene chloride (50 mL), and cold NaHCO3 (0.05M, 50 mL) is added to it. The reaction mixture is immediately extracted with methylene chloride (50 mL×3) and the organic extract is washed once with water and dried over anhydrous sodium sulphate. The solvent is removed to get 0.24 g of product. This compound is purified by column chromatography over silanized silica gel column to yield 0.135 g product (63%). (Purity>95%) M.p., 159°–163° C. Mass spectrum (FAB) m/e 925 [M+H]+. In the NMR spectrum (300 MHz, CDCl₃) the 7-H at 4.33 ppm in taxol appeared as a doublet of doublet at 5.65 ppm. The CH₃ group on the alanine moiety appears as a doublet at 1.27 ppm.

Elemental analysis: calculated for $C_{50}H_{58}N_2O \cdot .5 H_2O$ C, 61.91, H, 6.54, N, 2.89, Found C, 61.41, H, 6.59, N, 2.78%.

(c) Methanesulphonic acid salt of 7-(alanyl)taxol

To a solution of 7-(alanyl)taxol (62 mg, 0.658 mmol) in t-butanol (2 mL) and water (1 mL) cooled to 0°–5° C. is added methanesulphonic acid (6.39 mg, 2.13 mL, 3 mg/mL) and the mixture is stirred at this temperature for 2 minutes and filtered through a millipore filter (0.2M). the filtrate is freeze dried to get 66 mg product, M.P. 180°–184° C.

| Physical Properties | |
|---|---|
| Mol. Wt. | 1021 |
| M.P. | 180–184° C. (dec.) |
| Solubility | >2 mg/ml |
| HPLC operating conditions | |
| column: | RP-8, 150 mm length, 4.6 mm ID |
| mobile phase: | 0.02 M acetate (pH 5): Acetonitrile 50:50 containing 0.001 M tetrabutyl ammonium hydrogen sulphate |
| Detector: | Kratos spectroflow 757 |
| Flow rate: | 1 mL/min. |
| Ret. Volume | 8.7 mL |
| | 7.3 (taxol) |
| Plasma stability, 37° C.: | |
| conditions | t₁ (hrs.) |
| human plasma (20 μg/mL) | 11.9 |

EXAMPLE VI

Preparation of 2'-(alanyl)taxol (a) Synthesis of 2'(CBZ-L-Alanyl)taxol

To a solution of taxol (30 mg, 0.036 mmol) and CBZ.L.alanine (8.5 mg, 0.036 mmol) in methylene chloride (5 ml), DCC (45 mg) and 4-dimethylaminopyridine (4 mg) are added and the mixture is stirred at room temperature for 3 days. The reaction mixture is filtered and the solvent is removed from the filtrate. The residue is purified by preparative TLC over silanized silica gel plates and developed in ethyl acetate-petroleum ether 1:1 and the band above taxol is cut and eluted with ethyl acetate and solvent is removed to yield 28 mg 2'(CBZ-L-alanyl)taxol.

(b) Synthesis of 2'(alanyl)taxol by the deprotection of 2'(CBZ-L-analyl)taxol

2'(CBZ-L-alanyl)taxol is dissolved in ethanol in the presence of an organic acid such as acetic or formic acid and stirred at room temperature for 2 hrs in the presence of 5% paladium on carbon. The reaction mixture is filtered to remove the catalyst and solvent is removed. The crude product is dissolved in ethanol and petroleum ether is added to obtain the 2'(alanyl)taxol as the formate or acetate salt in low to moderate yield.

EXAMPLE VII

Preparation of 2'-(lysyl)taxol (a) Synthesis of 2'(N-di-t-boc-lysyl)taxol

To a mixture of taxol (30 mg, 0.035 mmol) and N-di.t-.boc-L-lysine (19 mg, 0.0368 mmol) in methylene chloride (10 mL) is added DCC (100 mg) and 4-dimethylaminopyridene (10 mg) and the mixture is stirred at room temperature for 2 days and filtered. Solvent is removed from the solvent. The residue is purified by preparative TLC on silanized silica gel plates and developed in ethyl acetate-petroleum ether 1:1, and the band above taxol is cut and eluted with ethyl acetate and solvent is removed to yield 20 mg product.

(b) Synthesis of 2'-(lysyl)taxol by the deprotection of t-boc group

The N-t-boc protected amino acid derivative of taxol is allowed to react with formic acid (99%, Sigma) at room temperature for 30–40 minutes. The excess formic acid is removed by evaporation under nitrogen. The crude material is purified by crystallization or chromatography to obtain N-deprotected amino acid derivative of taxol as the formate salt.

EXAMPLE VIII

Preparation of 2'-(L-alanyl)taxol (a) Synthesis of 2'(FMOC-L-alanyl)taxol

To a solution of taxol (60 mg, 0.072 mmol) and N-FMOC-L-alanine (22.4 mg) in methylene chloride (6 mL) is added DCC (60 mg) and 4-dimethylaminopyridene (2 mg) and the mixture is stirred at room temperature for two days and filtered. Solvent is removed from the filtrate. The crude material is purified by preparative TLC on silanized silica gel plates and developed in ethyl acetate-petroleum ether 1:2. The band above taxol is cut and eluted with methylene chloride and solvent is removed to get 48 mg product comprising 2'(FMOC-L-alanyl)taxol m.p. 162–64(dec).

(b) Deprotection of FMOC group of the protected amino acid derivative of taxol

The N-FMOC protected amino acid derivative of taxol is allowed to react with piperidine in methylene chloride for two hours and the solvent is removed. The residue is purified by chromatography to yield the deprotected amino acid derivative of taxol.

Pharmaceutical Preparations

The compounds of the invention can be formulated per se in pharmaceutical preparations or formulated in the form of pharmaceutically acceptable salts thereof, particularly as nontoxic pharmaceutically acceptable acid addition salts or acceptable basic salts. These salts can be prepared from the compounds of the invention according to conventional chemical methods.

Normally, the salts are prepared by reacting the free base or acid with stoichiometric amounts or with an excess thereof of the desired salt forming inorganic or organic acid in a suitable solvent or various combination of solvents. As an example, the free base can be dissolved in an aqueous solution of the appropriate acid and the salt recovered by standard techniques, for example, by evaporation of the solution. Alternatively, the free base can be dissolved in an organic solvent such as a lower alkanoyl, an ether, an alkyl ester, or mixtures thereof, for example, methanol, ethanol, ether, ethylacetate, an ethylacetate-ether solution, and the like, whereafter it is treated with the appropriate acid to form the corresponding salt. The salt is recovered by standard recovery techniques, for example, by filtration of the desired salt on spontaneous separation from the solution or it can be precipitated by the addition of a solvent in which the salt is insoluble and recovered therefrom.

The taxol derivatives of the invention can be utilized in the treatment of cancers, due to their cytotoxic, antitumor activity. The new compounds are administrable in the form of tablets, pills, powder mixtures, capsules, injectables, solutions, suppositories, emulsions, dispersions, food premix, and in other suitable form. The pharmaceutical preparation which contains the compound is conveniently admixed with a nontoxic pharmaceutical organic carrier or a nontoxic pharmaceutical inorganic carrier, usually about 0.01 mg up to 2500 mg, or higher per dosage unit, preferably 50–500 mg. Typical of pharmaceutically acceptable carriers are, for example, manitol, urea, dextrans, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid, and other conventionally employed acceptable carriers. The pharmaceutical preparation may also contain nontoxic auxiliary substances such as emulsifying, preserving, wetting agents, and the like as for example, sorbitan monolaurate, triethanolamine oleate, polyoxyethylene monostearate, glyceryl tripalmitate, dioctyl sodium sulfosuccinate, and the like.

Exemplary of a typical method for preparing a tablet containing the active agents is to first mix the agent with a nontoxic binder such as gelatin, acacia mucilage, ethyl cellulose, or the like. The mixing is suitably carried out in a standard V-blender and usually under anhydrous conditions. Next, the just prepared mixture can be slugged through conventional tablet machines and the slugs fabricated into tablets. The freshly prepared tablets can be coated, or they can be left uncoated. Representative of suitable coatings are the nontoxic coatings including shellac, methylcellulose, carnauba wax, styrene-maleic acid copolymers, and the like. For oral administration, compressed tablets containing 0.01 milligram, 5 milligrams, 25 milligrams, 50 milligrams, 500 milligrams etc., up to 2500 milligrams are manufactured in the light of the above disclosure and by art known fabrication techniques well known to the art and set forth in Remington's Pharmaceutical Science, Chapter 39, Mack Publishing Co., 1965.

To formulate the tablet, the active compound, cornstarch, lactose, dicalcium phosphate and calcium carbonate are uniformly blended under dry conditions in a conventional V-blender until all the ingredients are uniformly mixed together. Next, the cornstarch paste is prepared as a 10% paste and it is blended with the just prepared mixture until a uniform mixture is obtained. The mixture is then passed through a standard light mesh screen, dried in an anhydrous atmosphere and then blended with calcium stearate, and compressed into tablets, and coated if desired. Other tablets containing 10, 50, 100, 150 mgs, etc., are prepared in a like fashion.

The following Formulation I is an example of a tablet formulation comprising a compound of the invention.

| FORMULATION I | |
|---|---|
| Ingredients: | Per tablet, mg. |
| Active compound | 50.0 |
| Cornstarch | 15.0 |
| Cornstarch paste | 4.5 |
| Calcium carbonate | 15.0 |
| Lactose | 67.0 |
| Calcium stearate | 2.0 |
| Dicalcium phosphate | 50.0 |

The manufacture of capsules containing 10 milligrams to 2500 milligrams for oral use consists essentially of mixing the active compound with a nontoxic carrier and enclosing the mixture in a polymeric sheath, usually gelatin or the like. The capsules can be in the art known soft form of a capsule made by enclosing the compound in intimate dispersion within an edible, compatible carrier, or the capsule can be a hard capsule consisting essentially of the novel compound mixed with a nontoxic solid such as talc, calcium stearate, calcium carbonate, or the like. Capsules containing 25 mg, 75 mg, 125 mg, and the like, of the novel compound, singularly or mixtures of two or more of the novel compounds are prepared, for example, as follows:

| FORMULATION II | |
|---|---|
| Ingredients: | Per capsule, mg. |
| Active compound | 50.0 |
| Calcium carbonate | 100.0 |
| Lactose, U.S.P. | 200.0 |
| Starch | 130.0 |
| Magnesium stearate | 4.5 |

The above ingredients are blended together in a standard blender and then discharged into commercially available capsules. When higher concentrations of the active agent is used, a corresponding reduction is made in the amount of lactose.

The compounds of the invention can also be freeze dried and, if desired, combined with other pharmaceutically acceptable excipients to prepare formulations suitable for parenteral, injectable administration. For such administration, the formulation can be reconstituted in water (normal, saline), or a mixture of water and an organic solvent, such as propylene glycol, ethanol, and the like.

The dose administered, whether a single dose, multiple dose, or a daily dose, will of course, vary with the particular compound of the invention employed because of the varying potency of the compound, the chosen route of administration, the size of the recipient and the nature of the patient's condition. The dosage administered is not subject to definite bounds, but it will usually be an effective amount, or the equivalent on a molar basis of the pharmacologically active free form produced from a dosage formulation upon the metabolic release of the active drug to achieve its desired pharmacological and physiological effects. The dosage administered is generally in the range of 0.8 to 8 mg/kg of body weight or about 50–275 mg/m$^2$ of the patient, especially about 230–275 mg/m$^2$.

Biological Activity

As noted above, the taxol derivatives of the invention are useful for their antitumor activity. The compounds are particularly useful for the treatment of the same cancers for which taxol has been shown active, including human lung tumors, melanoma, leukemia, mammary tumors, and colon cancer.

The biological activity of the taxol derivatives has been tested by (A) in vitro studies to measure the microtubule assembly kinetics; and (B) in vitro studies on B16 melanoma cell culture kinetics; and (C) in vivo studies on SRC subrenal capsule xenograft of MX-1.

(A) In vitro Microtubule Assembly Kinetics Studies

Microtubules are an integral part of eukaryotic cells, and microtubule assembly is importantly associated with cell division and multiplication. It has been shown that microtubule polymerization is very sensitive to calcium; calcium can inhibit tubulin assembly and depolymerize preassembled microtubules. Known antitumor compounds have been studied for their effect on microtubule assembly.

Vinca alkaloids, such as vinblastine and vincristine, have been shown to disrupt cellular microtubules, i.e. in vitro they have been shown to inhibit microtubule assembly and to depolymerize steady state microtubules.

Similarly, colchicine has been shown to depolymerize microtubules in cells.

Taxol, on the other hand, has been shown to exhibit a very unique mechanism of action, in that it promotes the assembly of microtubules but inhibits their disassembly, thereby interfering with the $G_2$ and M phases of cell cycles and division. In vitro studies have shown that microtubules, once polymerized, in the presence of taxol resists depolymerization by other agents such as $CaCl_2$ or cold temperature which normally depolymerize microtubules.

The present inventors have conducted studies to investigate the effect of derivatives of taxol on the microtubule assembly. The microtubule assembly study was conducted using both 2' and 7-derivatives according to the in vitro procedures disclosed, for example, in Mellado et al., Biochemical and Biophysical Research Communications, Vol. 124, No. 2 (1984), pp. 329-336; Magri et al., J. Org. Chem., 51, 797-802 (1986); and Parness et al., Biochemical and Biophysical Research Communications, Vol. 105, No. 3, pp. 1082-1091 (1982). The ability of these compounds to assemble microtubules followed the order: taxol >7-(N,N-dimethylglycyl)taxol(11)>2'(N,N-diethylaminopropionyl)taxol(8)>2'(N,N-dimethylglycyl)taxol(2). This study shows that a free 2'-hydroxyl group is essential for microtubule assembly. The 2' derivatives are active only if the 2'-hydroxyl is rendered free during the course of the experiment. The 7-derivatives have free 2' hydroxyl and therefore, are active. This result is in good agreement with the activities of 2' and 7-acetyl taxol reported in the literature (Mellado et al., Biochemical & Biophysical Research Communications, vol. 124, No. 2 (1984) pp. 329-336.)

(B) In vitro B 16 Cell Culture Studies

To confirm the activity of the taxol derivatives of the invention, the present inventors conducted in vitro culture cell studies utilizing B-16 melanoma cells. These studies were conducted according to standard procedures as described in Donoso and Himes, Cancer Biochem. Biophysics, vol. 7, (1984), p. 133.

In the B-16 melanoma cell proliferation study, the order of effectiveness was found to be taxol>2'-(N,N-dimethylglycyl)taxol>2'-(N,N-diethylaminopropionyl)taxol> 7-(N,N-dimethylglycyl)taxol. This study and other kinetics studies indicate that the 2'derivatives revert back to taxol and exhibit activity. Therefore, 2'-derivatives probably act as prodrugs. On the other hand, 7-derivatives possess activity of their own and do not appear to act as prodrugs.

(C) In vivo Studies

The third type of experiment conducted to confirm the biological activity of the taxol derivatives comprised, in vivo studies in mice on subrenal capsule human mammary carcinoma MX-1 xenograft. The procedures followed are those described at pages 23-24 of NIH Publication No. 84-2635, In Vivo Cancer Model (February 1984).

Procedure

In the procedure, test groups of mice (6 mice per test group) and control groups of 12 mice per group are utilized. A tumor fragment (human mammary carcinoma MX-1 xenograft), is implanted under the membranous covering of the kidney of each mouse.

The following testing schedule is followed:
Day 0: Anesthetize animals. Record body weight (Weigh Day 1). Implant tumor, measure and record. Randomize animals after they recover from the anesthetic. Run bacterial cultures. Determine solubilities of test agent. Record deaths daily.

Day 1: Check cultures. Discard experiment if contaminated. Prepare test materials. Initiate test agent injections (in the nape of the neck) based on individual body weight. Treatment is Q4D on Days 1, 5, and 9. Prepare test agent fresh on each injection day and administer based on individual body weight for that day.

Day 2: Recheck cultures. Discontinue testing if contaminated and report accordingly.

Days 5 and 9: Prepare test agent fresh on each injection day and administer based on individual body weight for that day.

Day 11: End and evaluate experiment. Record body weights (Weigh Day 2). Measure tumor in OMU's (Ocular Micrometer Unit—10 OMU's=1 mm) and record.

Evaluation

The parameter measured is mean tumor weight change (delta) based on length and width measurements in millimeters. Mean animal body weights are computed for Day 1 and Day 11, compute T/C for all test groups with >65% survivors on Day 11. An excessive body weight change difference (test minus control) may also be used in evaluating toxicity. The dimensions are measured and recorded in Ocular Micrometer Units (OMU). A computer is utilized for the following:
(1) Converts OMU's to millimeters (mm).
(2) Calculates tumor weights (mgs) from tumor dimensions (mm×mm) following the formula for the volume of a prolate ellipsoid:

$$\frac{L \times W^2}{2}$$ Where $L$ is the longer of the two measurements.

(3) Calculates the change (delta) in mean tumor weight for each group of mice:
Change in Mean Tumor Weight=Mean Tumor Weight$_{FINAL}$−Mean Tumor Weight$_{INITIAL}$.
(4) Calculates the change (delta) in mean tumor weight for test (T) and control (C) groups.
(5) Calculates T/C% for all test groups with>65% survivors on Final Evaluation Day:

$$T/C \% = \frac{\Delta \, WtT}{\Delta \, WtC} \times 100 \text{ — if } \Delta \, WtT \text{ positive.}$$

$$T/C \% = \frac{\Delta \, WtT}{\text{Test Mean Tumor Weight}_{INITIAL}} \times 100 \text{ — if } \Delta \, WtT \text{ negative.}$$

Criteria for Activity

An initial T/C≦20% is considered necessary to demonstrate moderate activity. A reproducible T/C≦10% is considered significant activity.

Results

Results of the tests performed on several of the taxol derivatives are reported in Tables 1 and 2.

tions as would be obvious to one skilled in the art are intended to be included within the scope of the following claims.

We claim:

1. A compound of the formula

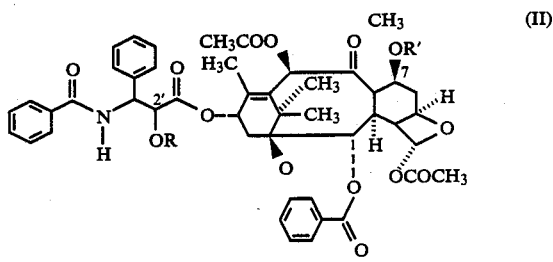

(II)

TABLE 1
HUMAN MAMMARY CARCINOMA TESTS RESULTS
AVERAGE TUMOR WEIGHTS

| | TREATMENT | | | INITIAL | | FINAL | | WEIGHT | # OF ANMLS | TEST BODY | ANML BODY |
|---|---|---|---|---|---|---|---|---|---|---|---|
| GRP NO. | COMPOUND NSC | DOSE (mg/kg) | % T/C | MGS | STD ERROR | MGS | STD ERROR | CHANGE (DELTA) | ALIVE CALC/TOTAL | WT CHG | WT DIFF |
| 0001 | Control | .00 | CNTL | .75 | .1 | 12.79 | 2.4 | 12.04 | 11/12 | | |
| 0102 | Taxol | 22.40 | TOX[b] | .60 | .1 | .00 | .0 | | 3/6 | −2.6 | −.9 |
| 0103 | " | 15.00 | CR[c] | .81 | .1 | .00 | .0 | −.81 | 6/6 | −4.2 | −2.5 |
| 0104 | " | 10.00 | −84 | .58 | .1 | .09 | .1 | −.49 | 6/6 | −2.0 | −.3 |
| 0105 | " | 6.67 | CR | .74 | .1 | .00 | .0 | −.74 | 5/5 | −1.5 | .2 |
| 0106 | " | 4.45 | CR | .79 | .1 | .00 | .0 | −.79 | 5/5 | −1.2 | .5 |
| 0207 | Cmpd 1[a] | 30.00 | TOX | .68 | .1 | .00 | | | 1/6 | −3.8 | −2.1 |
| 0208 | " | 20.00 | CR | .56 | .0 | .00 | .0 | −.56 | 4/6 | −2.2 | −.5 |
| 0209 | " | 13.30 | CR | .64 | .1 | .00 | .0 | −.64 | 4/6 | −2.3 | −.6 |
| 0210 | " | 8.90 | −53 | .77 | .1 | .36 | .4 | −.41 | 5/6 | −.9 | .8 |
| 0211 | " | 5.90 | −78 | .61 | .1 | .13 | .1 | −.48 | 6/6 | −2.2 | −.5 |

[a]Cmpd. 1 = 2'-(N,N-dimethylglycyl)taxol
[b]TOX indicates toxic level
[c]CR indicates complete remission of tumor

TABLE 2
HUMAN MAMMARY CARCINOMA TESTS RESULTS
AVERAGE TUMOR WEIGHTS

| | TREATMENT | | | INITIAL | | FINAL | | WEIGHT | # OF ANMLS | TEST BODY | ANML BODY |
|---|---|---|---|---|---|---|---|---|---|---|---|
| GRP NO. | COMPOUND NSC | DOSE (mg/kg) | % T/C | MGS | STD ERROR | MGS | STD ERROR | CHANGE (DELTA) | ALIVE CALC/TOTAL | WT CHG | WT DIFF |
| 0310 | Taxol | 15.00 | TOX[c] | .80 | .1 | | | | 0/5 | | |
| 0311 | " | 7.50 | TOX | .82 | .1 | .00 | .0 | | 3/5 | −1.7 | 2.3 |
| 0312 | " | 3.75 | CR[d] | .71 | .1 | .00 | .0 | −.71 | 4/5 | −2.9 | 1.1 |
| 0313 | " | 1.88 | 5 | .80 | .1 | 1.51 | 1.5 | .71 | 4/5 | −1.0 | 3.0 |
| 0001 | Control | .00 | CNTL | .77 | .1 | 15.38 | 2.2 | 14.61 | 10/11 | | |
| 0102 | Cmpd 7[a] | 33.00 | CR | .74 | .1 | .00 | .0 | −.74 | 4/5 | −2.7 | 1.3 |
| 0103 | " | 16.50 | −93 | .59 | .1 | .04 | .0 | −.55 | 3/4 | −5.7 | −1.7 |
| 0104 | " | 8.25 | 23 | .81 | .1 | 4.19 | 1.5 | 3.38 | 4/4 | −3.9 | .1 |
| 0105 | " | 4.13 | 34 | .74 | .1 | 5.66 | 1.3 | 4.92 | 4/5 | −4.5 | −.5 |
| 0206 | Cmpd 3[b] | 36.00 | TOX | .75 | .1 | | | | 0/5 | | |
| 0207 | " | 18.00 | CR | .82 | .1 | .00 | .0 | −.82 | 3/4 | −3.3 | .7 |
| 0208 | " | 9.00 | CR | .87 | .1 | .00 | .0 | −.87 | 5/5 | −2.7 | 1.3 |
| 0209 | " | 4.50 | CR | .78 | .1 | .00 | .0 | −.78 | 5/5 | −2.8 | 1.2 |

[a]Cmpd. 7 = 7-(N,N-dimethylglycyl)taxol
[b]Cmpd. 3 = HCl salt of 2'-(3-(N,N-diethylamino)propionyl)taxol
[c]TOX indicates toxic level
[d]CR indicates complete remission of tumor From these results, it can been seen that the taxol derivatives of the invention exhibit excellent antitumor activity. These compounds, therefore, are useful antitumor agents due to their biological activity and their increased water solubility as compared to taxol.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

wherein R and R' are each H or the residue of an amino acid selected from the group consisting of alanine, leucine, isoleucine, valine, phenylalanine, proline, lysine and arginine or a group of the formula

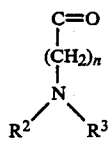

wherein n is an integer of 1 to 3 and $R^2$ and $R^3$ are each hydrogen or an alkyl radical having from one to three carbon atoms or wherein $R^2$ and $R^3$ together with the nitrogen atom to which they are attached form a saturated heterocyclic ring having four or five carbon atoms or an acid addition salt thereof, with the proviso that at least one of R and $R^1$ is not hydrogen, and with the second proviso that said compound is not 2'-(β-alanyl)taxol.

2. A compound according to claim 1, wherein at least one of R and R' is a member selected from the group consisting of L-alanine, L-leucine, L-isoleucine, L-valine, L-phenylalanine, L-proline, L-lysine, and L-arginine.

3. A compound according to claim 1, wherein at least one of R and R' is a group of the formula

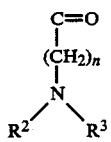

wherein n is an integer of from 1 to 3 and $R^2$ and $R^3$ are each an alkyl radical having from one to three carbon atoms.

4. A compound according to claim 1, which is 2'-(N,N-dimethylglycyl)taxol or an acid addition salt thereof.

5. A compound according to claim 1, which is 2'-(N,N-diethylaminopropionyl)taxol or an acid addition salt thereof.

6. A compound according to claim 1, which is 7-(N,N-dimethylgylcyl)taxol, or an acid addition salt thereof.

7. A compound according to claim 1, which is 2',7-di(N,N-dimethylglycyl)taxol, or an acid addition salt thereof.

8. A compound according to claim 1, which is 7-(alanyl)taxol or an acid addition salt thereof.

9. A pharmaceutical composition comprising an effective antitumor amount of at least one compound of the formula

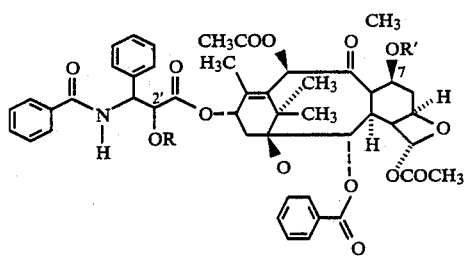

wherein R and R' are each H or the residue of an amino acid selected from the group consisting of alanine, leucine, isoleucine, valine, phenylalanine, proline, lysine and arginine or a group of the formula

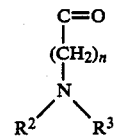

wherein n is an integer of 1 to 3 and $R^2$ and $R^3$ are each hydrogen or an alkyl radical having from one to three carbon atoms or wherein $R^2$ and $R^3$ together with the nitrogen atom to which they are attached form a saturated heterocyclic ring having four to five carbon atoms, with the proviso that at least one of R and $R^1$ is not hydrogen, or a pharmaceutically acceptable salt thereof, and a pharmaceutically acceptable carrier, diluent or excipient.

10. A pharmaceutical composition according to claim 9, wherein said at least one compound is 2'-(N,N-dimethylglycyl)taxol.

11. A pharmaceutical composition according to claim 10, wherein said at least one compound is 2'-(N,N-diethylaminopropionyl)taxol.

12. A method for treating tumors which comprises administering to a patient an effective antitumor amount of at least one compound according to claim 1.

13. A method according to claim 12, wherein said treatment comprises treating tumors selected from the group consisting of human lung tumors, melanoma, leukemia, mammary tumors and colon cancer.

14. A compound according to claim 1, which is 7-(N,N-dimethylaminopropionyl)taxol or an acid addition salt thereof.

15. A compound according to claim 1, which is 2'-(L-alanyl)taxol or an acid addition salt thereof.

16. A compound according to claim 1, which is 2'-(L-lysyl)taxol or an acid addition salt thereof.

17. A compound according to claim 1, which is 7-(L-lysyl)taxol or an acid addition salt thereof.

18. A pharmaceutical composition according to claim 9, wherein said at least one compound is 7-(N,N-dimethylglycyl)-taxol.

19. A pharmaceutical composition according to claim 9, wherein said at least one compound is 2'7-di-(N,N-diethylaminopropionyl)taxol.

20. A pharmaceutical composition according to claim 9, wherein said at least one compound is 7-(N,N-diethylaminopropionyl)taxol.

21. A pharmaceutical composition according to claim 9, wherein said at least one compound is 2'-(L-alanyl)-taxol.

22. A pharmaceutical composition according to claim 9, wherein said at least one compound is 7-(L-alanyl)-taxol.

23. A pharmaceutical composition according to claim 9, wherein said at least one compound is 2'-(L-lysyl)-taxol.

24. A pharmaceutical composition according to claim 9, wherein said at least one compound is 7-(L-lysyl)-taxol.

25. A taxol derivative selected from the group consisting of
2'-(N,N-diethylaminopropionyl)taxol;
2'-(N,N-dimethylglycyl)taxol;
7-(N,N-dimethylglycyl)taxol;
2',7-di-(N,N-dimethylglycyl)taxol;
7-(N,N-diethylaminopropionyl)taxol;
2'-(L-lysyl)taxol;

7-(L-lysyl)taxol; and acid addition salts thereof.

26. A compound according to claim 25, wherein the acid addition salt is a methanesulphonic acid salt.

27. A compound according to claim 25, wherein the acid addition salt is an HCl salt.

28. A compound according to claim 25, which 2'-(N,N-diethylaminopropionyl)taxol methanesulphonic acid salt.

29. A compound according to claim 25, which is 2'-(N,N-diethylaminopropionyl)taxol HCl salt.

30. A pharmaceutical composition comprising an effective antitumor amount of at least one compound according to claim 25, and a pharmaceutically acceptable carrier.

31. A pharmaceutical composition according to claim 30, wherein said compound is 2'-(N,N-diethylaminopropionyl)taxol methanesulphonic acid salt or 2'-(N,N-diethylaminopropionyl)taxol HCl salt.

32. A method for treating tumors which comprises administering to a patient an effective antitumor amount of at least one compound according to claim 25.

33. A method for treating tumors which comprises administering to a patient an effective antitumor amount of at least one compound according to claim 28.

34. A method for treating tumors which comprises administering to a patient an effective antitumor amount of at least one compound according to claim 29.

* * * * *

UNITED STATES PATENT AND TRADEMARK OFFICE
CERTIFICATE OF CORRECTION

PATENT NO. : 4,960,790
DATED : October 2, 1990
INVENTOR(S) : Valentino J. Stella and Abraham E. Mathew It is certified that error appears in the above-identified patent and that said Letters Patent is hereby corrected as shown below:

Column 1, please insert the following on line 5, after the title.

--This invention was made with government support under N01-CM-67912 awarded by the National Institutes of Health. The government has certain rights in the invention. --

Signed and Sealed this

Thirtieth Day of November, 1993

Attest:

BRUCE LEHMAN

Attesting Officer

Commissioner of Patents and Trademarks